United States Patent [19]

Gyer et al.

[11] Patent Number: 4,458,544
[45] Date of Patent: Jul. 10, 1984

[54] SAMPLE SUPPLY SYSTEM AND THE HANDLING OF SAMPLES

[75] Inventors: John F. Gyer, Clarksboro; Donald K. Mosher, Glassboro, both of N.J.

[73] Assignee: Mobil Oil Corporation, New York, N.Y.

[21] Appl. No.: 356,585

[22] Filed: Mar. 9, 1982

[51] Int. Cl.³ ............................................. G01N 1/14
[52] U.S. Cl. .............. 73/864.21; 73/864.87; 222/390; 422/67; 422/68
[58] Field of Search ........... 73/864.21, 864.82, 864.87, 73/863.31; 422/67, 68; 222/136

[56] References Cited

U.S. PATENT DOCUMENTS

| | | | |
|---|---|---|---|
| 3,143,393 | 8/1964 | Des Hons | 422/67 X |
| 3,754,443 | 8/1973 | Harris, Sr. et al. | 73/864.21 X |
| 3,841,160 | 10/1974 | Iwao | 73/864.87 |
| 4,038,874 | 8/1977 | Baldwin et al. | 73/864.87 X |
| 4,077,395 | 3/1978 | Woolner | 128/762 |
| 4,116,067 | 9/1978 | Pankratz et al. | 73/863.31 |
| 4,279,361 | 7/1981 | Chung | 222/390 X |
| 4,316,466 | 2/1982 | Babb | 604/73 X |

Primary Examiner—Daniel M. Yasich
Attorney, Agent, or Firm—Alexander J. McKillop; Michael G. Gilman; Laurence P. Hobbes

[57] ABSTRACT

A sample supply system for the supply of successive samples of fluent material to a sample receiving zone, the system including a displaceable magazine having a plurality of locating stations for locating sample receptacles on the magazine; a sample receiving zone for receiving samples of fluent material discharged from such sample receptacles; and a discharge member adapted to be actuated to apply pressure to a fluent material contained in a sample receptacle for discharging fluent material; the magazine being displaceable relatively to the sample receiving zone and the discharge member to bring any locating station into register with the sample receiving zone and the discharge member for the discharge of fluent material from a receptacle located at such locating station.

36 Claims, 3 Drawing Figures

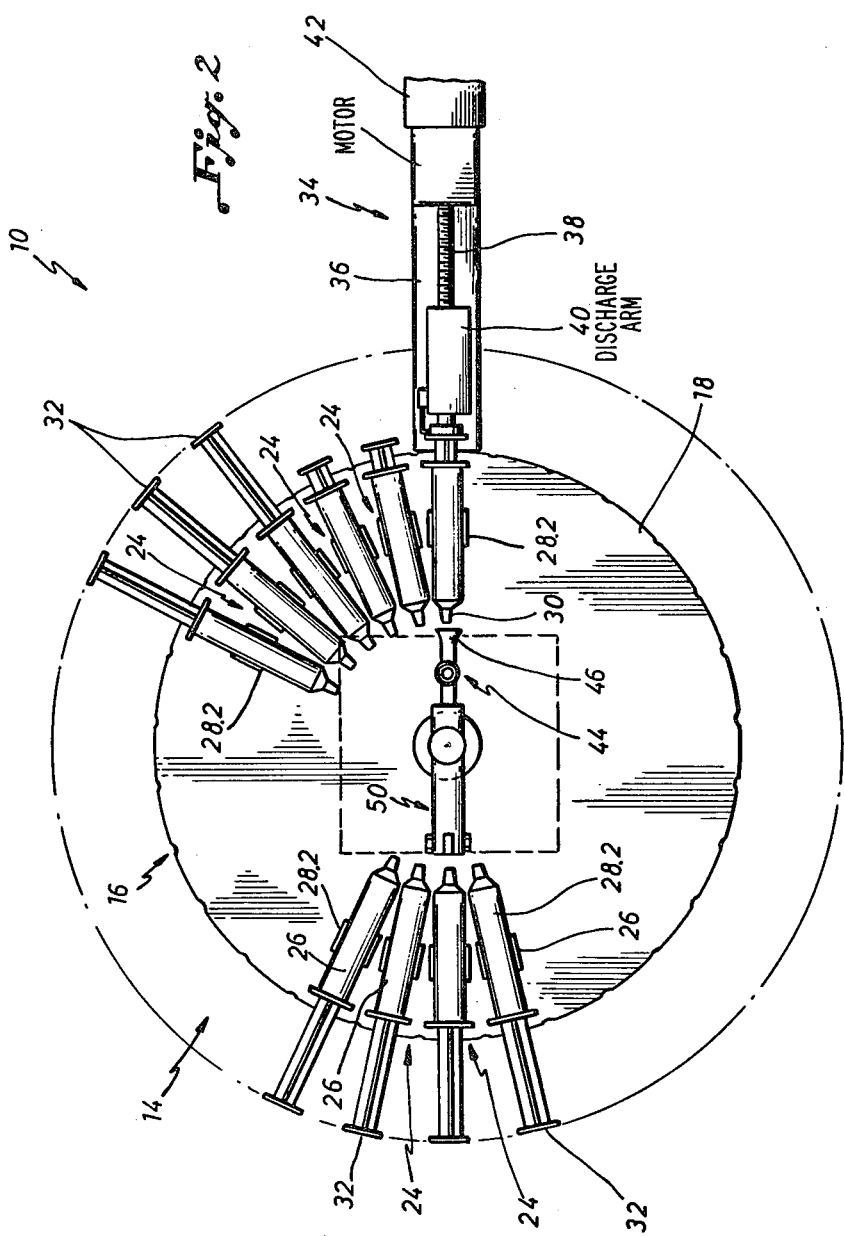

SAMPLE SUPPLY SYSTEM AND THE HANDLING OF SAMPLES

This invention relates to a sample supply system and to the handling of samples.

Various systems are employed for the supply of successive samples of fluent materials which are to be analyzed, tested or otherwise handled. Many of these systems are relatively clumsy and labor intensive, requiring virtual constant supervision and attendance. Many of these systems are systems in which samples are supplied manually. Many of these systems are systems in which contamination of succeeding samples by the remnants of preceding samples is difficult to avoid. This is particularly the case where pumps are employed to pump samples selectively into a common manifold, or where large volume suction systems are employed to draw successive samples into a handling zone.

In the determination of the viscosity of lubricating oils, successive samples of such oils are usually placed in a sample chamber of a viscometer such as a cold cranking simulator (hereinafter referred to as a CCS).

The samples are usually supplied manually by means of a pipette or syringe.

After each test the sample chamber and rotor must be purged and cleaned. The CCS is usually purged and bathed in hot water, whereafter it is washed with naptha and then with acetone. Thereafter it is dried.

Since naptha and acetone are both of relatively low viscosity with respect to oils, solvent residues will introduce errors. In addition, both naptha and acetone create undesirable vapors in laboratory environments.

It is accordingly one object of this invention to provide a system to overcome or reduce at least some of these disadvantages.

According to one aspect of this invention there is provided a sample supply system for the supply of successive samples of fluent material to a sample receiving zone, the system comprising:
(a) a magazine having a plurality of locating stations for locating sample receptacles on the magazine;
(b) a sample receiving zone for receiving samples of fluent material discharged from such sample receptacles; and
(c) a discharge member adapted to be actuated to apply pressure to a fluent material contained in a sample receptacle for discharging fluent material;
the magazine being displaceable relatively to the sample receiving zone and the discharge member to bring any locating station into register with the sample receiving zone and the discharge member for the discharge of fluent material from a receptacle located at such locating station.

The discharge member may be a member of any suitable type for its required purpose, and may be a member actuated by any appropriate means. Thus, for example, the discharge member may produce fluid pressure or mechanical pressure to act on fluent material contained in a sample receptacle.

In an embodiment of the invention, the discharge member may comprise a discharge arm which is adapted to be displaced relatively to a locating station to apply pressure to a fluent material in a receptacle located at such station. The discharge arm may conveniently be adapted to displace a displaceable wall such as a diaphragm or plunger associated with a fluent material receptacle located on a locating station.

In a preferred embodiment of the invention, the discharge member includes a screw assembly to which the discharge arm is connected, with the screw assembly being adapted to be rotatably driven to advance and retract the discharge arm.

The system may preferably include a motor for driving the discharge member and a controller for controlling operation of the motor.

The motor may preferably be in the form of a linear stepping motor, while the controller may be in the form of a computer or a microprocessor which is programmed to operate the motor in a required mode.

The magazine may conveniently be displaceable by being in the form of a rotatable member adapted to be rotatably driven to position the locating stations selectively in register with the discharge member and the sample receiving zone. Alternatively, the magazine may, for example, comprise a displaceable flexible belt, a conveyor or endless belt, a displaceable carriage or rack, or the like.

The magazine preferably has the locating stations arranged in a circumferentially spaced annular arrangement, and preferably has locating means associated with or adapted to be associated with the locating stations for locating sample receptacles on the locating stations. While sample receptacles may be permanently mounted on the rotatable member, they are preferably removably mounted thereon to allow ready replacement of samples, and to allow used sample receptacles to be discarded or cleaned.

The locating means may, for example, comprise an annular locating ring having recesses for accommodating or engaging with sample receptacles. The ring may be displaceable or removable. Alternatively, the locating means may comprise locating members mounted on the magazine at the locating stations.

The system preferably includes a motor for driving the magazine, with the motor being controlled by the controller to bring the locating stations successively into register with the discharge member in a predetermined order.

The sample receiving zone may conveniently comprise a guide tube to guide discharged fluent material from a discharge zone to a handling zone.

In a preferred embodiment of the invention the guide tube has a guide inlet at one end and a guide outlet at its other end, and is displaceable between an operative position where its guide inlet can register with a discharge outlet of a receptacle located at a registering locating station, and an inoperative position where its guide inlet will be spaced from such a receptacle discharge outlet to permit relative movement of the guide tube and the magazine.

The system may include any suitable displacement member for displacing the guide tube between its operative and inoperative conditions. The displacement member may, for example, be in the form of a motor, an air piston, or the like.

The system preferably includes purging means for purging the system between successive samples. The purging means may conveniently be a vacuum or pressure operated purging system which can be selectively actuated to purge the operative portion of the system, or selected portions thereof, during use.

The system may include an analytical instrument for the analysis of fluent materials, operatively associated therewith for the system to supply successive samples of fluent material to be analyzed.

The analytical instrument may be an instrument of any conventional type which requires successive samples of fluent materials for analysis, testing, calibration or handling. In an embodiment of the invention the analytical instrument may be a viscometer, a viscometer in the form of a cold cranking simulator (CCS), or a viscometer in the form of a high shear rate viscometer.

The invention further extends to a sample supply system for the supply of successive samples of fluent material, the system comprising:
 (a) a magazine having a plurality of locating stations for locating sample receptacles on the magazine;
 (b) a displaceable guide tube adapted to be selectively displaced for engaging with a discharge outlet of a receptacle to receive a sample discharged from such receptacle and guide such sample to a handling zone; and
 (c) a discharge member adapted to be actuated to discharge fluent material from a fluent material receptacle located at a locating station,
the magazine being displaceable to bring any locating station into register with the guide tube and the discharge member for the discharge of a sample of fluent material from a sample receptacle located at such locating station.

The invention further extends to a viscometer system for determining the viscosity of liquids, the viscometer system comprising:
 (a) a sample chamber for receiving a liquid to be analyzed;
 (b) a rotor adapted to be rotatably driven in the sample chamber;
 (c) a chamber inlet leading to the sample chamber;
 (d) a guide tube having a guide outlet to communicate with the chamber inlet, and having a guide inlet, the guide tube being displaceable between an inoperative position and an operative position;
 (e) a displaceable magazine having a plurality of spaced locating stations for locating sample receptacles on the magazine, the magazine being displaceable to selectively bring any locating station into register with the guide tube for the guide tube inlet to be engaged with a discharge outlet of a sample receptacle when located at such locating station; and
 (f) a discharge member aligned with the guide tube for discharging a sample of liquid from a sample receptacle into the guide tube.

In a specific example of the invention, the viscometer may be in the form of a cold cranking simulator such as, for example, the cold cranking simulator model CCS2 supplied by Cannon Instrument Co.

The invention further extends to an analytical instrument for analysis of samples of fluent material, the instrument including a sample supply system for supplying samples of fluent materials to be tested to the instrument, the sample supply system comprising:
 (a) a displaceable magazine having a plurality of locating stations for holding syringe type receptacles for containing fluent material to be analyzed;
 (b) guide means for guiding samples of material dispensed from syringe type receptacles when located on the locating stations, to the instrument;
 (c) a discharge member comprising a displaceable piston for engaging with a plunger of a syringe receptacle to displace such plunger for dispensing fluent material;
 (d) magazine drive means for driving the magazine to selectively bring a locating station into register with the discharge member and the guide means; and
 (e) discharge drive means for displacing the piston between operative and inoperative positions.

The invention still further extends to a method of supplying samples of liquid to an analytical instrument for analysis, the method comprising:
 (a) supplying a first sample of liquid to the instrument;
 (b) removing the sample to purge the instrument;
 (c) supplying a second sample of the same liquid to the instrument;
 (d) analyzing the second sample;
 (e) continuing the supply of the same liquid to the instrument to compensate for sample loss during analysis;
 (f) discontinuing the supply of that liquid;
 (g) removing the sample to purge the instrument; and
 (h) commencing a corresponding cycle with the next liquid.

While the sample supply system of this invention may have various applications, it has particular application where a number of successive samples of fluent material must be supplied to a receiving zone or instrument, and where contaimination between successive sample is undesirable. The invention therefore has particular application in regard to viscometers, and more specifically in regard to viscometers for use in establishing the viscosity of lubricating oils and the like.

An embodiment of the invention is now described by way of example with reference to the accompanying drawings.

BRIEF DESCRIPTION OF THE DRAWINGS

In the drawings:

FIG. 2 shows a diagrammatic, fragmentary, sectional plan view of the system of FIG. 1 along line II—II: except that the system of FIG. 2 has an alternative form of locating means.

Figure 1:
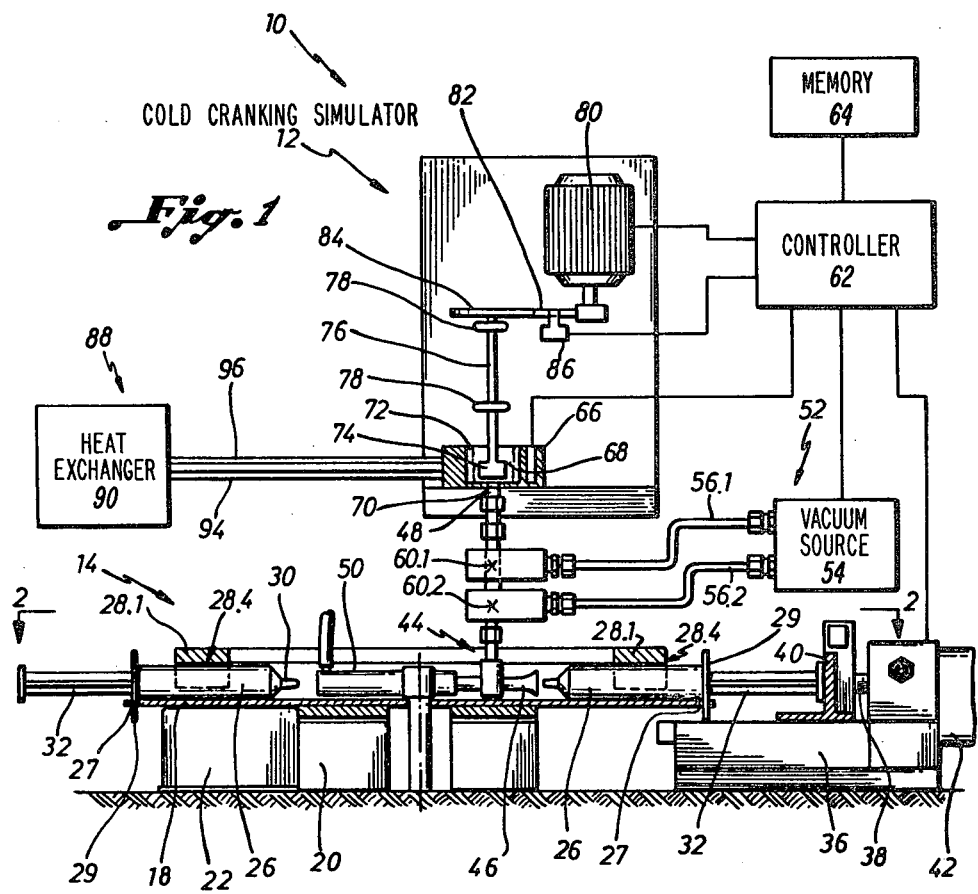
FIG. 1 shows a diagrammatic side elevation of a viscometer system in accordance with this invention, the viscometer system comprising a cold cranking simulator and a sample supply system.
Figure 3:
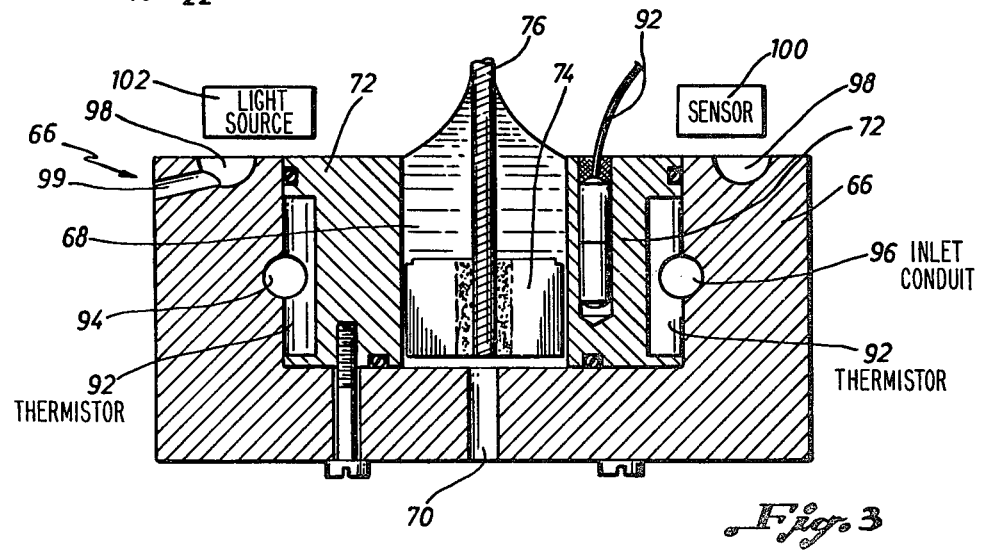
FIG. 3 shows, to an enlarged scale, a crosssectional side elevation of the sample chamber of the cold cranking simulator of FIGS. 1 and 2.

With reference to the drawings, reference numeral 10 refers generally to a viscometer system in accordance with this invention. The viscometer system 10 comprises a viscometer in the form of a cold cranking simulator (CCS) 12 and a sample supply system 14 for supplying samples of fluent materials in the form of lubricating oil to the cold cranking simulator (CCS) 12 for determination of the viscosity of such samples.

The sample supply system 14 comprises a magazine 16 which is displaceable by being in the form of an annular turntable 18 which is rotatably supported on a base 20. A magazine motor 22 is mounted on the base 20 for rotatably driving the turntable 18. The magazine motor is preferably in the form of a linear stepping motor.

The annular turntable 18 has a plurality of circumferentially spaced locating stations 24 which are arranged in an annular band for supporting a plurality of sample receptacles 26 in appropriate predetermined positions on the turntable 18.

The system 14 includes locating means for locating the sample receptacles 26 at the locating stations. The locating means comprises circumferentially extending slots 27 which are provided in the turntable 18 at each locating station for receiving a flange 29 of each receptacle 26 to thereby locate the receptacles radially on the turntable 18.

The locating means further comprises an annular locating ring 28.1 in FIG. 1. The ring 28.1 has semicircular recesses 28.4 in its downwardly directed surface to receive the receptacles 26 and locate them circumferentially at the locating stations 24. The ring 28.1 further has locator pins (not shown) for engaging with corresponding holes in the turntable to locate the ring 28.1 in its appropriate orientation on the turntable 18. The ring 28.1 may be lifted slightly to allow removal or insertion of receptacles 26.

Each sample receptacle 26 is in the form of a syringe of conventional type, having a discharge outlet 30, and having a displaceable plunger 32.

The syringes 26 are preferably in the form of disposable syringes which may be filled with samples of fluent materials to be tested, and may then be discarded after use thereby eliminating the labor costs involved in cleaning sample receptacles, and positively avoiding contamination of succeeding samples by preceding samples.

The sample supply system 14 further comprises a discharge member 34 which is mounted in position and is adapted to be actuated for discharging samples of liquid from the syringes 26 during use.

The discharge member 34 comprises a housing 36 within which a screw assembly 38 is mounted. A displaceable discharge arm 40 is mounted on the screw assembly 38. The screw assembly 38 is adapted to rotatably driven to advance the discharge arm 40 in a longitudinal direction towards the center of the turntable 18, or to retract the discharge arm 40.

The discharge member 34 further includes discharge member drive means in the form of a linear stepping motor 42 for driving the screw assembly 38.

The discharge member 34 is mounted so that the turntable 18 can be rotatably displaced relatively thereto, and so that when any locating station 24 is in register with the discharge member 34, displacement of the discharge arm 40 will cause the discharge arm 40 to engage with a plunger 32 and to advance such plunger 32 for discharging liquid from the syringe 26 located at such locating station 24.

The sample supply system 14 further comprises a sample receiving zone in the form of a guide tube 44 to guide discharged samples of liquids to a handling zone in the form of a cold cranking simulator 12.

The guide tube 44 has a guide inlet 46 and a guide outlet 48.

The guide tube 44 is displacable between its inoperative position as shown in the drawings, and an operative position where its guide inlet 46 can register with and engage with a discharge outlet 30 of a syringe 26 which is located on a locating station 24 in register with the discharge member 34 and the guide tube 44.

The sample supply system 14 includes a displacement member 50 for displacing the guide tube 44 between its operative and inoperative positions. The displacement member 50 preferably comprises an air piston of any conventional type which is actuable to displace the guide tube 44 into its operative position, and which can be deactivated for a spring incorporated in the member 50, to return the guide tube 44 to its inoperative position.

The sample supply system 14 further includes purging means 52 for purging the viscometer system 10 between successive samples.

The purging means 52 comprises a vacuum source 54 to provide a purging effect. The purging means 52 further comprises a first purging conduit 56.1 and a second purging conduit 56.2. The first purging conduit 56.1 extends from the vacuum source 54 to one end of a purging section of the guide tube 44 proximate its guide outlet 48, while the second purging conduit 56.2 extends from the vacuum source 54 to an opposed end of the purging section of the guide tube 44 proximate the guide inlet 46.

A first three-way valve 60.1 is provided at the junction of the first purging conduit 56.1 and the guide tube 44, whereas a second three-way valve 60.2 is provided at the junction of the second purging conduit 56.2 and the guide tube 44.

The first and second three-way valves can be operated selectively for purging of the system. Thus, for example, the second three-way valve 60.2 may be closed while the first three-way valve 60.1 may be open to permit purging from the guide tube 44 on the downstream side of the second three-way valve, and at the same time to permit purging from the CCS 12. Thereafter, the first three-way valve 60.1 may be closed while the second three-way valve 60.2 is opened to permit purging from the upstream side of the guide tube 44 upstream of the first three-way valve.

In an alternative arrangement, the first three-way valve 60.1 may be opened to permit purging from the downstream side of that valve, and the second three-way valve 60.2 may be opened to permit purging from the upstream side of that valve. Therefore, both parts can be purged at the same time.

The viscometer system 10 further comprises a controller 62 which incorporates a memory 64. The controller 62 may be in the form of a computer or a microprocessor of any appropriate type. The controller 62 is operatively connected to the motor 42 of the discharge member, to the magazine motor 22, to the air piston of the displacement member 50, and to the vacuum source 54 to thereby effectively and automatically control operation of the sample supply system 14.

The guide outlet 48 of the guide tube 44 is connected to the CCS 12 for supplying samples of lubricating oils contained in the syringes 26 to the CCS for viscosity determination.

The CCS 12 comprises a sample chamber 66 for receiving samples of fluid for determining the viscosity of such samples. The sample chamber has a sample cavity 68 into which these samples are fed for the viscosity determination, and has an inlet conduit 70 leading to the sample cavity 68. The guide outlet 48 of the guide tube 44 is connected to the inlet conduit 70.

The sample chamber 66 includes a stator 72 which defines the sample cavity 68.

The CCS 12 further includes a rotor 74 which is rotatably mounted on a shaft 76 which is rotatably supported in bearings 78. The shaft 76 is flexible below the lower bearing 78.

The CCS 12 further comprises a variable speed, substantially constant torque electric motor 80 which drives a belt 82. The belt is mounted on a pulley 84 which is mounted on the shaft 76 for the motor 80 to drive the rotor 74.

A speed indicator device 86 is provided in a position to be driven by the belt 82 for giving an indication of the rate of rotation of the rotor 74.

The motor 80 is connected to the controller 62 for control thereby.

The speed indicator device 86 is likewise connected to the controller 62 so that the controller 62 may indicate the viscosity of the liquid.

The CCS 12 also includes temperature means 88 for maintaining the cavity 68 at a desired temperature during a series of tests. The temperature means 88 includes a heat exchanger 90 which is coupled by means of an outlet conduit 94 and an inlet conduit 96 to an annular jacket 92 which surrounds the stator 72. The temperature means 88 further includes thermistors 92 for measuring the temperature and for controlling the temperature of the temperature means 88. The thermistors 92 are also connected to the controller 62 for automatic indication and control of the temperature.

The stator 72 is provided with an annular groove 98 which surrounds the sample cavity 68 for receiving overflow liquid which overflows from the cavity 68 during use. The groove 98 is connected to a waste conduit 99 for leading waste liquid to a dump zone.

In the embodiment illustrated in FIG. 2, an alternative form of locating means is shown to the locating means 28.1 of FIG. 1. In FIG. 2, the locating means comprises a plurality of locating members 28.2 which are mounted on the locating stations 24. Each locating member 28.2 comprises a spring clamp for removably clamping a syringe 26 on its locating station 24.

In use, disposable syringes 26 are filled with the lubricant oils to be tested and are then located on the turntable 18 by means of the locating means 28. The controller 62 may then be set to control rotation of the turntable 18 and thus the order in which the syringes 26 will be brought into register with the discharge member 34 and guide tube 44.

When a selected syringe 26 has been displaced into its registering position by the turntable 18, the controller 62 will actuate the displacement member 50 to engage the guide inlet 46 with the discharge outlet 30 of that positioned syringe 26.

Thereafter the controller 62 will operate the discharge member 34 to cause the screw assembly 38 to be rotated by the stepping motor 42 to advance the discharge arm 40 into engagement with the plunger 32 of that syringe 26.

At the appropriate time the controller 62 will cause the motor 42 to advance the discharge arm 40 at a predetermined high speed to discharge a sample of the liquid contained in that syringe 26 into the guide tube 44 and through to the sample cavity 68 to fill the cavity 68.

The controller 62 will then stop further advance of the discharge arm 40, will open the first and second three-way valves 60.1 and 60.2, and will actuate the purging means 52 to purge that first sample from the sample cavitiy 68 and from the guide tube 44.

Thereafter the controller 62 will reset both the first and second three-way valves 60 into their positions where they permit flow through the guide tube 44, and will again actuate the motor 42 to again rapidly advance the discharge arm 40 for discharging a second purging sample of material through the guide tube 44 and into the cavity 68. Thereafter the controller 62 will again control the three-way valves to purge that sample from the system thereby cleaning the system and removing a significant proportion of the remains of previous samples tested in the system.

Thereafter the controller 62 will again rapidly advance the discharge arm 40 to discharge a third sample through the guide tube 44 into the cavity 68. This will be sample which is used for determining the viscosity thereof in the CCS 12.

Once the viscosity of that sample has been determined at the desired temperature in accordance with conventional means by driving the rotor 74, determining the rate of 1 rotation of the rotor and recording that rate to indicate the viscosity of the liquid, the controller 62 will again operate the purging system to purge the sample from the cavity 68 and from the guide tube 44.

Thereafter the controller 62 will control the magazine motor 22 to rotate the turntable 18 and bring a succeeding syringe 26 into register with the guide tube 44 and the discharge member 34.

Because certain motor oils contain polymers which undergo phase changes at low temperatures, certain viscoelastic samples tend to spiral towards the rotor shaft 76 when the rotor 74 is being rotatably driven. This viscoelastic effect causes the sample to climb from the shear zone in the cavity 68 thereby resulting in a lesser charge of sample in the cavity 68. This diminished volume of sample in the cavity 68 as a result of such loss of sample will cause the rotor speed to increase thereby giving a false indication of the apparent viscosity of the sample.

For such motor oils or lubricants which exhibit a viscoelastic effect, the controller 62 will be programmed to drive the discharge member 34 at a slow rate after the sample to be tested has been discharged through the guide tube into the cavity 68.

The discharge arm 40 will therefore be advanced at a slow rate to continue to supply lubricating oil from the same syringe 26 through the guide tube 44 and into the cavity 68 to replace the lubricating oil which is drawn out of the cavity 68 as a result of the viscoelastic effect. This will therefore balance the volume of fluid being tested in the cavity 68 so that the rotor speed will give a sufficiently accurate indication of the viscosity of the sample. The overflow of lubricating fluid from the cavity 68 as a result of the viscoelastic effect, will flow into an annular groove 98 provided around the cavity 68. The overflow into the annular groove 98 will flow away through a discharge trough 99.

To aid in controlling the supply of compensating lubricating oil to compensate for oil loss through the viscoelastic effect, the system 10 includes a sensor 100 and a light source 102. The sensor 100 is electrically connected to the controller 62 so that the sensor 100 may sense the extent of the viscoelastic effect and the controller 62 may thus control the rate at which the liquid is supplied by the discharge member 34 to compensate for the liquid loss in the cavity 68 from the viscoelastic effect.

By controlling operation of the discharge member 34 so that the first, or first and second purging samples, and the sample to be tested are discharged rapidly, reduces the time involved in running each test. Thereafter the slow discharge to compensate for the viscoelastic effect can be run at a rate to balance the rate of loss of liquid from the cavity 68. The embodiment of the invention as illustrated in the drawings therefore provides the advantage that samples of fluids to be tested can readily be loaded into standard syringes at a location remote from the viscometer system 10. These samples can then readily be located in position on the locating stations 24 of the turntable 18 when desired. They can be located in a required order or, if desired, the controller 62 can be programmed to bring the syringes 26 into register with the discharge member 34 in an appropriate order.

The controller 62 can then automatically control all operations of the sample supply system 14 and of the CCS 12 thereby dispensing with the need for constant supervision and attendance.

The invention provides the further advantage that by incorporating an automatic purging system, and using one or more charges of a succeeding sample to purge the system of the preceding sample, the remnants of the preceding sample can be effectively removed without the use of undesirable cleaning procedures and fluids. In addition, any remnants of a preceding sample remaining after purging, would in any event be more compatible with the sample being tested than would be the case where cleaning fluids of much lower viscosities are employed as in the prior art procedures.

By using individual syringes which are actuated from outside the receptacles 26, contamination is reduced substantially. This is particularly so when compared to the prior art systems in which large pump or vacuum systems are employed to dispense the materials to be tested. In these systems the large pump systems, manifold systems or suction systems, which present relatively large surface areas in relation to the volumes of the sample, have to be cleaned. This is therefore much more tedious and substantially increases the possibility of contamination of succeeding samples by precedings samples.

The embodiment as illustrated in the drawings provides the further advantage that a large number of samples can be tested sequentially either in a predetermined or a random order, as may be required.

The embodiment of the invention will therefore save manpower, improve precision by having an accurately controlled discharge rate and volume, and by speeding up the rate at which tests can be done.

While the embodiment as illustrated with reference to the drawings, is a viscometer system 10, it will be appreciated that the sample supply system of this invention can equally be incorporated or used with other instruments and systems which require or use samples of fluent materials which are dispensed periodically. This is particularly the case for instruments or systems which require constant volumes of samples at substantially constant or at several substantially constant rates.

We claim:

1. A sample supply system for the supply of successive samples of fluent material to a sample receiving zone of an analytical instrument for the analysis of fluent materials, the system comprising:
   (a) a magazine having a plurality of locating stations for locating sample receptacles on the magazine;
   (b) a displaceable quide tube adapted to be selectively displaced for engaging with a discharge outlet of one of said sample receptacles on the magazine to receive a sample discharged from said receptacle and guide said sample to a handling zone; and
   (c) a discharge member adapted to be actuated by a controller to discharge fluent material from a fluent material receptacle located at a one of said locating stations said member comprising a discharge arm which mechanically displaced in a longitudinal direction relatively to one of said locating stations to apply pressure to a means so as to thereby apply pressure to the fluent material in said receptacle the located at said station;
   the magazine being displaceable to bring said locating station at said sample receiving zone into register with the guide tube and the discharge member for the discharge of said sample of fluent material from the sample receptacle located at said locating station.

2. A sample supply system for the supply of successive samples of fluent material to a sample receiving zone of an analytical instrument for the analysis of fluent materials, the system comprising:
   (a) a magazine having a plurality of locating stations for locating sample receptacles on the magazine;
   (b) a sample receiving zone for receiving samples of fluent material discharged from said sample receptacles; and
   (c) a discharge member adapted to be actuated by a controller to apply pressure to the fluent material contained in one of said sample receptacles for discharging the fluent material, said member comprising a discharge arm which is adapted to be mechanically displaced in a longitudinal direction relatively to one of said locating stations to apply pressure to a means so as to thereby apply pressure to the fluent material in said receptacle located at said station;
   the magazine being displaceable relatively to the sample receiving zone and the discharge member to bring said locating station at said sample receiving zone into register with the sample receiving zone and the discharge member for the discharge of fluent material from the receptacle located at said locating station.

3. A system according to claim 1, in which the discharge arm is adapted to be displaced to displace a displaceable wall associated with the fluent material receptacle located on said locating station at said receiving zone.

4. A system according to claim 2 or claim 3, in which the discharge member includes a screw assembly to which the discharge arm is connected, with the screw assembly being adapted to be rotatably driven to advance and retract the discharge arm.

5. A system according to claim 4, including a motor for driving the screw assembly.

6. A system according to claim 5, including a controller for controlling operation of the motor, the controller being programmed to drive the screw assembly to discharge a first purging sample from a receptacle and then to discharge a first handling sample to be handled from the same receptacle.

7. A system according to claim 6, in which the controller is programmed to drive the screw assembly to discharge a first purging sample of a fluent material at a high speed, then to discharge a first handling sample of the same material at a high speed, and then to continue the discharge of the same fluent material at a low speed for compensating for fluent material loss resulting from a viscoelastic effect.

8. A system according to claim 2, in which the magazine comprises a rotatable member which is adapted to be rotatably driven to position the locating stations selectively in register with the discharge member and the sample receiving zone.

9. A system according to claim 8, in which the rotatable member comprises an annular turntable having circumferentially spaced locating stations and having locating means for locating receptacles on the spaced locating stations.

10. A system according to claim 9, in which the locating means comprises slots provided at the locating stations for receiving flanges extending from sample receptacles to locate such receptacles on the locating stations.

11. A system according to claim 9 or claim 10, in which the locating means comprises locating members in the form of clamps for removably clamping receptacles at the locating stations.

12. A system according to claim 11, in which the clamps are spring clamps which are mounted at the locating stations, and which are shaped to clamp syringe type receptacles at the locating stations.

13. A system according to claim 9 or claim 10, in which the locating means comprises an annular locating ring having a plurality of circumferentially spaced downwardly directed recesses for receiving sample receptacles to thereby locate such receptacles at the locating stations when the ring is positioned on the turntable.

14. A system according to claim 8, including a motor for driving the rotatable member, and including a controller for controlling operation of the motor to bring the locating stations successively into register with the discharge member in a predetermined order.

15. A system according to claim 2, in which the sample receiving zone comprises a guide tube to guide discharged fluent material to a handling zone.

16. A system according to claim 15, in which the guide tube has a guide inlet at one end and a guide outlet at its other end, and in which the guide tube is displaceable between an operative position where its guide inlet can register with a discharge outlet of a receptacle located at a registering locating station and an inoperative position where its guide inlet would be spaced from such a receptacle discharge outlet.

17. A system according to claim 16, including a displacement member for displacing the guide tube between its operative and inoperative positions.

18. A system according to claim 15, claim 16 or claim 17, in which the guide tube has a purging section intermediate its ends, and in which the system includes purging means for purging the guide tube of fluent material between successive discharges of fluent materials.

19. A system according to claim 18, in which the purging means comprises a first purging conduit extending from the purging section for connection to a suction source, and a first valve between the purging section and the first purging conduit, the first valve being operable to selectively purge the guide tube.

20. A system according to claim 19, in which the purging means further comprises a second purging conduit and a second valve, in which the second purging conduit extends from the purging section proximate one end of the guide tube, in which the first purging conduit extends from the purging section proximate an opposed end of the guide tube, and in which the first and second valves are selectively operable to purge selected parts of the guide tube.

21. A system according to claim 2, including an analytical instrument for analysis of fluent materials, the instrument being adapted to be provided with successive samples of fluent materials discharged to the sample receiving zone.

22. A system according to claim 21, in which the analytical instrument comprises a viscometer.

23. A system according to claim 22, in which the viscometer comprises a cold cranking simulator.

24. A system according to claim 22, in which the viscometer comprises a high shear rate viscometer.

25. A system according to claim 21 or claim 22, including a controller for controlling operation of the magazine, discharge member and sample receiving zone, and for controlling operation of the analytical instrument to analyze successive samples of fluent materials.

26. An analytical instrument for analysis of samples of fluent material, the instrument including a sample supply system for supplying samples of fluent materials to be tested to the instrument, the sample supply system comprising:
(a) a displaceable magazine having a plurality of locating stations for holding syringe type receptacles for containing fluent material to be analyzed;
(b) guide means for guiding samples of material dispensed from syringe type receptacles when located on the locating stations, to the instrument;
(c) a discharge member comprising a selectively activated displaceable piston for engaging with a plunger of a syringe receptacle to displace such a plunger for dispensing fluent material;
(d) magazine drive means for driving the magazine to selectively bring a locating station into register with the discharge member and the guide means;
(e) discharge drive means for displacing the piston between operative and inoperative positions; and
(f) control means for controlling selective operation of the magazine drive means and the discharge drive means.

27. A sample supply system for the supply of successive samples of liquid or fluent material to a handling zone, the system comprising:
(a) a magazine adapted to be rotatably displaced, the magazine being adapted to support a plurality of sample receptacles at spaced intervals at locating stations thereon;
(b) a guide tube having a guide inlet and a guide outlet, the guide tube being displaceable between an operative position for its guide inlet to register with a discharge outlet of a receptacle located at a locating station, and an inoperative position;
(c) a discharge member adapted to be actuated for discharging said liquid from a sample receptacle positioned at a locating station, said member comprising a discharge arm which is adapted to be mechanically displaced in a longitudinal direction relatively to one of said locating stations to apply pressure to a means so as to thereby apply pressure to the fluent material in said receptable having the fluent material therein located at said station;
(d) magazine drive means for driving the magazine to bring said locating station into register with the guide tube and the discharge member;
(e) discharge drive means for driving the discharge member to discharge liquid from a receptacle;
(f) guide tube drive means for displacing the guide tube between its operative and inoperative positions; and
(g) control means for controlling operation of the magazine drive means, the discharge drive means and the guide tube drive means.

28. A system according to claim 27, in which the control means comprises a computer or microprocessor programmed to control the drive means to bring a locating station into register, to displace the guide tube into its operative position, and to discharge successive samples of a liquid at intervals from a sample receptacle.

29. A system according to claim 28, in which the control means is programmed to discharge a first purging sample from a receptacle, to then discharge a first handling sample from the same receptacle, and to then continue the discharge from the same receptacle at a lower speed to combat any viscoelastic effect of discharged fluid when analyzed in a viscometer.

30. A system according to claim 29, including purging means for removing such a first purging sample by suction before a first handling sample is discharged.

31. A viscometer system for determining the viscosity of liquids, the viscometer system comprising:
    (a) a sample chamber for receiving a liquid to be analyzed;
    (b) a rotor adapted to be rotatably driven in the sample chamber;
    (c) a chamber inlet leading to the sample chamber;
    (d) a guide tube having a guide outlet to communicate with the chamber inlet, and having a guide inlet, the guide tube being displaceable between an inoperative position and an operative position;
    (e) a displaceable magazine having a plurality of spaced locating stations for locating sample receptacles on the magazine, the magazine bing displaceable to selectively bring any one of the locating station into register with the guide tube for the guide tube inlet to be engaged with a discharge outlet of a sample receptacle when located at said locating station; and
    (f) a discharge member aligned with the guide tube for discharging a sample of the liquid from a sample receptacle into the guide tube.

32. A system according to claim 31, including a variable speed, substantially constant torque motor for driving the rotor, including drive means for driving the magazine, drive means for displacing the guide tube, and drive means for displacing the discharge member, and including a controller programmed to control operation of the respective drive means.

33. A system according to claim 31 or claim 32, in which the viscometer is in the form of a cold cranking simulator.

34. A method of supplying samples of liquid to an analytical instrument for analysis, wherein said sample is supplied to a sample receiving zone by means of a system comprising a sample receptacle from which a liquid or fluent material is discharged by means of a discharge member adapted to be actuated so as to be displaced in a longitudinal direction relative to said sample receptacle to apply pressure to a means so as to thereby apply pressure to the fluent material contained in said sample receptacle in order to discharge said fluent material, said sample receptacle being located on a magazine having a plurality of locating stations for locating sample receptacles on the magazine, the method comprising:
    (a) supplying a first sample of one the liquid in one of said receptacles to said instrument;
    (b) removing the sample by suction to purge the instrument;
    (c) supplying a second sample of the said liquid to the instrument;
    (d) analyzing the second sample;
    (e) continuing the supply of the said liquid to the instrument to compensate for sample loss during analysis resulting from a viscoelastic effect attributable to sample phase changes;
    (f) discontinuing the supply of said liquid;
    (g) removing the liquid by suction to purge the instrument; and
    (h) commencing a corresponding cycle with the next liquid.

35. A method according to claim 34, in which the first and second samples are supplied at a higher speed, while the continuing supply of liquid is effected at a lower speed, commensurate with the loss of sample resulting from a viscoelastic effect attributable to sample phase changes.

36. A method according to claim 34 or claim 35, which comprises supplying at least one further purging sample between the first and second samples, and removing the purging sample.

* * * * *

UNITED STATES PATENT AND TRADEMARK OFFICE
CERTIFICATE OF CORRECTION

PATENT NO. : 4,458,544
DATED : JULY 10, 1984
INVENTOR(S) : JOHN F. GYER et al.

It is certified that error appears in the above-identified patent and that said Letters Patent is hereby corrected as shown below:

Column 9, line 57, "quide" should read -- guide --.

Column 9, line 65, insert -- , -- after "stations"

Column 9, line 66, insert -- is -- after "which"

Column 13, line 28, "bing" should read -- being --.

Signed and Sealed this

Fourth Day of June 1985

[SEAL]

Attest:

DONALD J. QUIGG

Attesting Officer  Acting Commissioner of Patents and Trademarks